US006608683B1

(12) United States Patent
Pilgrim et al.

(10) Patent No.: US 6,608,683 B1
(45) Date of Patent: Aug. 19, 2003

(54) ACOUSTIC RESONANCE PHASE LOCKED PHOTOACOUSTIC SPECTROMETER

(75) Inventors: Jeffrey S. Pilgrim, Santa Fe, NM (US); David S. Bomse, Santa Fe, NM (US); Joel A. Silver, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 36 days.

(21) Appl. No.: 09/782,137

(22) Filed: Feb. 12, 2001

Related U.S. Application Data

(60) Provisional application No. 60/181,610, filed on Feb. 10, 2000.

(51) Int. Cl.[7] ............................................... G01N 21/00
(52) U.S. Cl. .................... 356/432; 356/437; 250/339.09
(58) Field of Search ................................ 356/432, 437, 356/441; 250/343, 339.09; 73/24.02

(56) References Cited

U.S. PATENT DOCUMENTS

| | | | |
|---|---|---|---|
| 3,938,365 A | * 2/1976 | Dewey, Jr. et al. | ......... 73/24.02 |
| 4,051,371 A | * 9/1977 | Dewey, Jr. et al. | ..... 250/339.09 |
| 4,051,372 A | * 9/1977 | Aine | ........................... 250/343 |
| 4,200,399 A | * 4/1980 | Kimble et al. | .............. 356/437 |
| 4,738,536 A | * 4/1988 | Kitamori et al. | ............ 356/441 |
| 5,129,255 A | * 7/1992 | Corbin | ....................... 73/24.02 |
| 5,159,411 A | * 10/1992 | Hammerich et al. | ........ 356/432 |

FOREIGN PATENT DOCUMENTS

JP 9-133655 A * 5/1997

OTHER PUBLICATIONS

Angeli, G.Z., et al., "Design and Characterization of a Windowless Resonant Photoacoustic chamber Equipped with Resonance Locking Circuitry," *Rev. Sci, Instrum.*, vol. 62, No. 3, pp 810–813 (Mar. 1991).

Pao, Y–H, Editor "Signal Generation Detection" from Optoacoustic Spectroscopy and Detection, Academic Press, New York (1977) pp 20–22. No Month Available.

Thony, A., et al., "New Developments in $Co_2$–Laser Photoacoustic Monitoring of Trace Gases," *Infrared Phys. Technol.*, vol. 36, No. 2, pp 585–615 (1995). No Month Available.

* cited by examiner

*Primary Examiner*—Michael G. Lee
*Assistant Examiner*—Jared J. Fureman
(74) *Attorney, Agent, or Firm*—Jeffrey D. Myers

(57) ABSTRACT

A photoacoustic spectroscopy method and apparatus for maintaining an acoustic source frequency on a sample cell resonance frequency comprising: providing an acoustic source to the sample cell to generate a photoacoustic signal, the acoustic source having a source frequency; continuously measuring detection phase of the photoacoustic signal with respect to source frequency or a harmonic thereof; and employing the measured detection phase to provide magnitude and direction for correcting the source frequency to the resonance frequency.

17 Claims, 2 Drawing Sheets

ACOUSTIC RESONANCE PHASE LOCKED PHOTOACOUSTIC SPECTROMETER

CROSS-REFERENCE TO RELATED APPLICATIONS

This application claims the benefit of the filing of U.S. Provisional Patent Application Serial No. 60/181,610, entitled "Acoustic Resonance Frequency Locked Photoacoustic Spectrometer", filed on Feb. 10, 2000, and the specification thereof is incorporated herein by reference.

A related application entitled "Acoustic Resonance Frequency Locked Photoacoustic Spectrometer" is being filed concurrently herewith, to Jeffrey S. Pilgrim et al., U.S. patent application Ser. No. 09/782,138, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. DE-FG03-99ER82887 awarded by the U.S. Department of Energy.

BACKGROUND OF THE INVENTION

1. Field of the Invention (Technical Field)

The present invention relates to high-sensitivity detection of contaminants in gases by optical techniques generally termed photoacoustic spectroscopy (PAS) or optoacoustic spectroscopy.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Photoacoustic spectroscopy is a known technique for high sensitivity detection of trace gases. Absorption by the target species of incident optical energy results in a transient heating of the gas. If the incident optical energy is modulated then the gas is periodically heated which creates a time-varying pressure wave or sound. The sound can be measured with a microphone.

PAS is often enhanced through the use of acoustically resonant gas cells. These cells build up sound intensity at the resonance frequencies. Depending on the type of noise dominant in the system, resonant cells can dramatically improve signal-to-noise ratios and thereby, the measurement sensitivity. Individual and combination acoustic resonance modes including longitudinal, radial, and azimuthal are often utilized. Unfortunately, resonance frequencies depend on the local speed of sound which can change with temperature and gas composition. In addition, changes in cell dimensions due to mechanical stress can change these resonance frequencies. Thus, for a practical resonance-based photoacoustic spectrometer, it is necessary to maintain the modulation frequency at the acoustic resonance frequency.

The ability to maintain the optical source modulation frequency or its harmonics on an acoustic resonance frequency of a photoacoustic cell will hereafter be referred to as resonance frequency locking. In field measurements, microphone noise is not usually a photoacoustic instrument's sensitivity-limiting noise source. When microphone noise is not the limiting noise source, operation on an acoustic resonance enhances the signal-to-noise ratio. *Optoacoustic Spectroscopy and Detection*, Y-H Pao, ed. (Academic Press, New York, 1977), pps. 20–22. Because there is a 1/f dependence of the photoacoustic signal on frequency, operation at a resonance frequency represents a compromise between the enhancement, or Q, of the resonance cell and higher frequency operation. Thus, resonant operation is usually desirable provided the resonance frequency is not so high that the 1/f penalty outweighs the cavity Q. For example, a cell with a resonance at 8000 Hz with a Q of 200 would generate the same signal, all other parameters being equal, as a non-resonant cell operating at 40 Hz. In many systems, there is less background acoustic noise at 8000 Hz than at 40 Hz; resonant operation at 8000 Hz then provides a better signal-to-noise ratio.

Acoustic resonances may have narrow bandwidths. As the amplification factor (or resonance cavity Q) increases for a given frequency, the bandwidth gets narrower. Thus, as sensitivity is increased by improving the acoustic quality of the photoacoustic cell, the need for a method to maintain the acoustic modulation frequency on resonance increases proportionately. For example, a cell with a Q of 200 at 8000 Hz will have a bandwidth of 40 Hz. Thus, a change of the resonance frequency of only 20 Hz will reduce the signal by a factor of 2. A change of 20 Hz can be caused by a temperature change of less than 1 degree C. at room temperature.

The present invention achieves continuous, real-time acoustic resonance frequency locking by utilizing the behavior of the detection phase of the acoustic signal with respect to the acoustic resonance. For purposes of the specification and claims, "detection phase" means phase angle of a detected signal with respect to the local oscillator reference for the lock-in amplifier (or like device) having a fixed phase relationship to the optical source modulation frequency or its harmonics. The detection phase is sensitive to the slope of the resonance response of the cell at the acoustic modulation frequency. Thus, the detection phase is qualitatively the derivative of the acoustic resonance line shape. A zero crossing of the detection phase occurs on the line center of the acoustic resonance. The value of the measured detection phase can then be used to adjust the acoustic modulation frequency so as to drive the phase back towards zero. The measured detection phase provides an error signal for the location of the cell acoustic resonance. As the acoustic resonance frequency drifts with temperature, gas composition, change in cell dimensions, etc., the acoustic modulation frequency will be continually updated and maintained to match the cell acoustic resonance frequency.

This method for acoustic resonance frequency locking can be used to equal effectiveness regardless of the method of producing photoacoustic signal. In traditional PAS the optical source radiation is amplitude modulated (AM). The modulation can be achieved by means of a mechanical chopper, a shutter, an acousto-optic modulator, or modulation of a (e.g., semiconductor) pump waveform. Other methods for achieving an amplitude modulated optical source are contemplated by and fall within the invention. In addition, Southwest Sciences, Inc. has implemented wavelength modulation spectroscopy (WMS) with PAS detection, as described in U.S. patent application Ser. No. 09/687,408. With WMS, the optical radiation source is modulated in wavelength, not amplitude (if WMS is implemented with injection current modulation of a diode laser, AM results only as a side-effect). Nevertheless, WMS produces a synchronous amplitude modulated pressure wave at the microphone. Because the present acoustic line-locking mechanism depends on features of the cell acoustic resonance and not the source of the sound, it is equally applicable to AM and WMS-based PAS.

A source of acoustic power independent of PAS generation (a speaker) has previously been used to implement an acoustic frequency locking mechanism. M. W. Sigrist and coworkers generated sound at a resonance frequency of a PAS cell with a speaker whose frequency was locked to the cell resonance via the microphone's detection phase at the resonance frequency. G. Z. Angeli, et al., "Design and characterization of a windowless resonant photoacoustic chamber equipped with resonance locking circuitry" *Rev. Sci. Instrum.* 62, 810 (1991). The locked resonance frequency was used to generate an amplitude modulated optical frequency for PAS generation. The optical source modulation operated at a separate cell resonance that was a constant fraction of the frequency used for resonance locking. Several disadvantages of this approach are apparent. The method requires a separate acoustic source independent of the PAS generation source. The method introduces sound at frequencies other than that where the PAS signal occurs. This sound must be attenuated in order to prevent overloading of the detection microphone. Depending on the acoustic source spectral purity, noise may be induced at the PAS detection frequency. The method relies on the PAS resonance frequency and the acoustic source generated locking frequency changing in the same way in a dynamic environment. If the cell geometry changes differently for the two frequencies (due, for example, to a mechanical stress), the frequency ratio will not be constant and the lock will be lost.

In their description, Sigrist and coworkers teach away from using phase as a mechanism for acoustic resonance frequency locking. Their teaching is based on the so-called kinetic cooling effect observed for some gases. The kinetic cooling effect introduces a phase differential for PAS signal generated from some gaseous molecules relative to the signal phase that might be produced by other types of gaseous molecules. Thus, certain combinations of molecules at specific concentration ratios where their respective PAS signal amplitudes are comparable may introduce a concentration dependent PAS signal phase shift that is independent of the phase shift caused by the acoustic modulation frequency with respect to the PAS cell acoustic resonance frequency. This teaching is not applicable to the vast majority of circumstances encountered by a trace gas detection instrument. Many applications involve the detection of a single gaseous species in a bath of another gas. Since the instrument would not be configured to detect the bath gas, only one type of gaseous molecule will contribute to the PAS signal detection phase and the instrument would be optimized for that molecule. The kinetic cooling effect is not relevant in this case. Secondly, their are many combinations of types of gaseous molecules where each type contributes to the measured detection phase in the same way. Thus, no concentration dependent phase shift is produced for those combinations and the kinetic cooling effect is not relevant. Finally, in an instrument configured for a specific gaseous molecule (i.e., PAS signal detection phase optimized for that molecule), the presence of another type of gaseous molecule which produces a different PAS signal detection phase can be accommodated without loss of resonance locking fidelity providing that it is present in low concentration or its concentration is constant.

M. W. Sigrist and coworkers also implemented a type of acoustic resonance maintenance by scanning over the cell resonance. A. Thony, et al., "New Developments in $CO_2$-Laser Photoacoustic Monitoring of Trace Gases", *Infrared Phys. Technol.* 36, 585 (1995). Their method consisted of a slow scan of several discrete steps over the cell resonance. The PAS signal vs. acoustic frequency was fit to an inverted parabolic curve and the peak of the fit used as the resonance line center. The acoustic modulation frequency was then corrected to coincide with the calculated resonance line center. This method was then repeated approximately every 20 minutes. This is not a real-time resonance frequency lock. If the cell resonance drifted during the 20 minute interval between measurements, the PAS source modulation frequency would not correspond to the cell resonance frequency. In addition, sample signal acquisition is halted during the resonance scan measurement and fitting. Continuous sample measurement is precluded in this approach. The method has utility is removing very slow drift effects, but does not provide high-fidelity resonance locking for a dynamically changing PAS sample environment. Contrast that with the present invention, whereby continual maintenance of zero detection phase with respect to the cell resonance provides a real-time error signal for perpetual operation on the cell resonance with continuous PAS sample analysis.

SUMMARY OF THE INVENTION
(DISCLOSURE OF THE INVENTION)

The present invention is of a photoacoustic spectroscopy method and apparatus for maintaining an acoustic source frequency on a sample cell resonance frequency comprising: providing an acoustic source to the sample cell to generate a photoacoustic signal, the acoustic source having a source frequency; continuously measuring detection phase of the photoacoustic signal with respect to the source frequency or a harmonic thereof; and employing the measured detection phase to provide magnitude and direction for correcting the source frequency to the resonance frequency. In the preferred embodiment, sound is generated from absorption of optical power by a species inside the sample cell, preferably amplitude or wavelength modulated optical power. The invention can thus be used with a flowing gas species. Sound may also be generated from a speaker. A metric proportional to acoustic power inside the cell (as well as to concentration of an absorption species) is measured, preferably at the acoustic source frequency or a harmonic thereof.

The invention is also of an acoustic resonance frequency locked photoacoustic spectrometer comprising: a source generating a photoacoustic signal, the source having a source frequency; and a lock-in amplifier employing a detection phase of the photoacoustic signal with respect to the source frequency or a harmonic thereof, and whereby the amplifier maintains the photoacoustic signal on a resonance frequency of a sample cell.

A primary object of the present invention is to provide for continuous, real-time, acoustic resonance frequency locking in PAS.

A primary advantage of the present invention is that it can operate at high frequencies and can be used in measurement of flowing gaseous species.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is of a method and apparatus for maintaining a continuous, real-time acoustic modulation frequency on a sample cell resonance of a photoacoustic spectrometer. The invention comprises:

(a) Providing a photoacoustic sample cell with its associated geometry-determined acoustic resonances. The cell incorporates a mechanism for detecting acoustic power such as a microphone;

(b) Providing an acoustic source to the photoacoustic sample cell. Such source may be the sound produced by the absorption of optical power by a species inside the photoacoustic cell. The optical power may be amplitude or wavelength modulated. Alternatively, a source separate from the photoacoustic effect, such as a speaker, can be employed to provide acoustic power to the cell;

(c) Employing a mechanism to continuously monitor the detection phase of the PAS signal with respect to the acoustic source frequency or its harmonics; and (d) Using the measured detection phase to provide magnitude and direction for correction of the acoustic source frequency so that the acoustic source frequency is maintained to match a photoacoustic cell resonance.

The invention provides a commercially-viable solution for a resonant photoacoustic spectrometer for trace gas detection. The performance of the acoustic resonance locked spectrometer is superior to devices where the acoustic source frequency is allowed to deviate from the cell acoustic resonance. A resonant PAS cell according to the invention allows for operation with a flowing gas sample. In order to provide comparable signal-to-noise ratios to our design, a non-resonant cell would have to operate at substantially lower frequencies where flowing gas samples are precluded due to flow noise obscuring PAS signals.

The invention improves photoacoustic spectroscopy using resonant acoustic cells by providing acoustic resonance frequency stabilization (resonance frequency locking). Resonance frequency locking is critical when the local speed of sound varies or the cell dimensions change. Variation in the local speed of sound can occur by temperature drifts and transients caused, for example, by someone walking by the photoacoustic spectrometer. As an additional example, varying temperature is encountered in measurements of atmospheric gas (such as water vapor) on weather balloons. Changes in sample gas composition can also affect the local speed of sound (e.g., humid air has a different speed of sound than dry air). Thus, for continuous monitoring in a resonant photoacoustic spectrometer with a variable gas sample, resonance frequency locking is an enabling technology.

Figure 1:
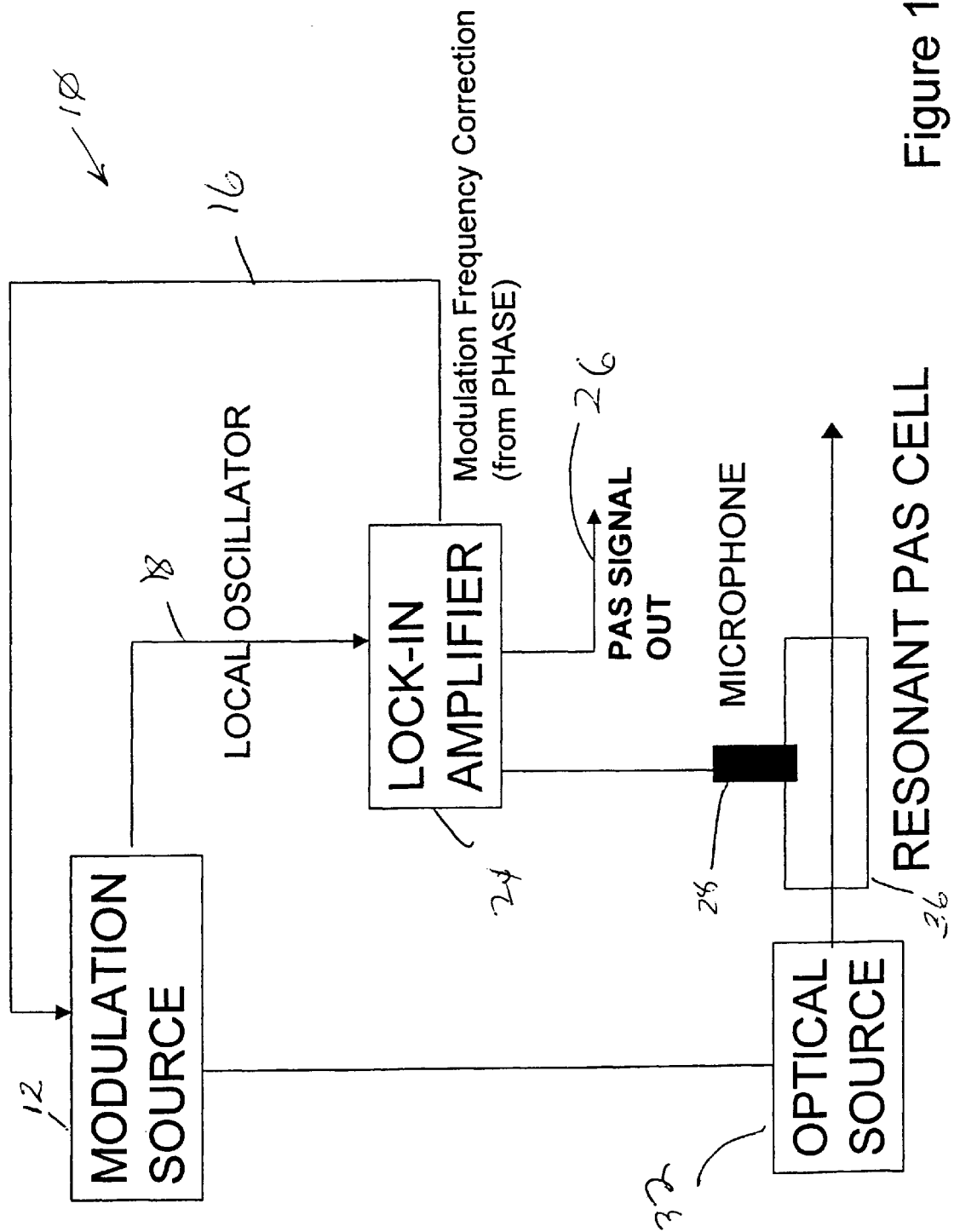
FIG. 1 is a schematic diagram of the preferred embodiment of the invention.

The preferred embodiment of the present invention 10 is shown schematically in FIG. 1. An optical source 32 is directed into a photoacoustic cell 30. The cell may be of any size or shape. It should be recognized that for any cell, there will be a set of characteristic resonance frequencies. It is preferred to use cylindrically symmetric cells for maximum enhancement of radial and longitudinal acoustic resonances. However, other types of resonances (azimuthal, Helmholtz, etc.) and combinations or overtones of resonances are contemplated by the present invention. The optical source in FIG. 1 is modulated so as to provide a periodic heating of the gaseous sample contained within the photoacoustic cell. The modulated heating generates a sound wave that is detected using a microphone 28. The invention preferably includes modulation source 12 which generates local oscillator 18, and lock-in amplifier 20 generating modulation frequency correction (from phase) 16 and PAS signal out 26.

Figure 2:
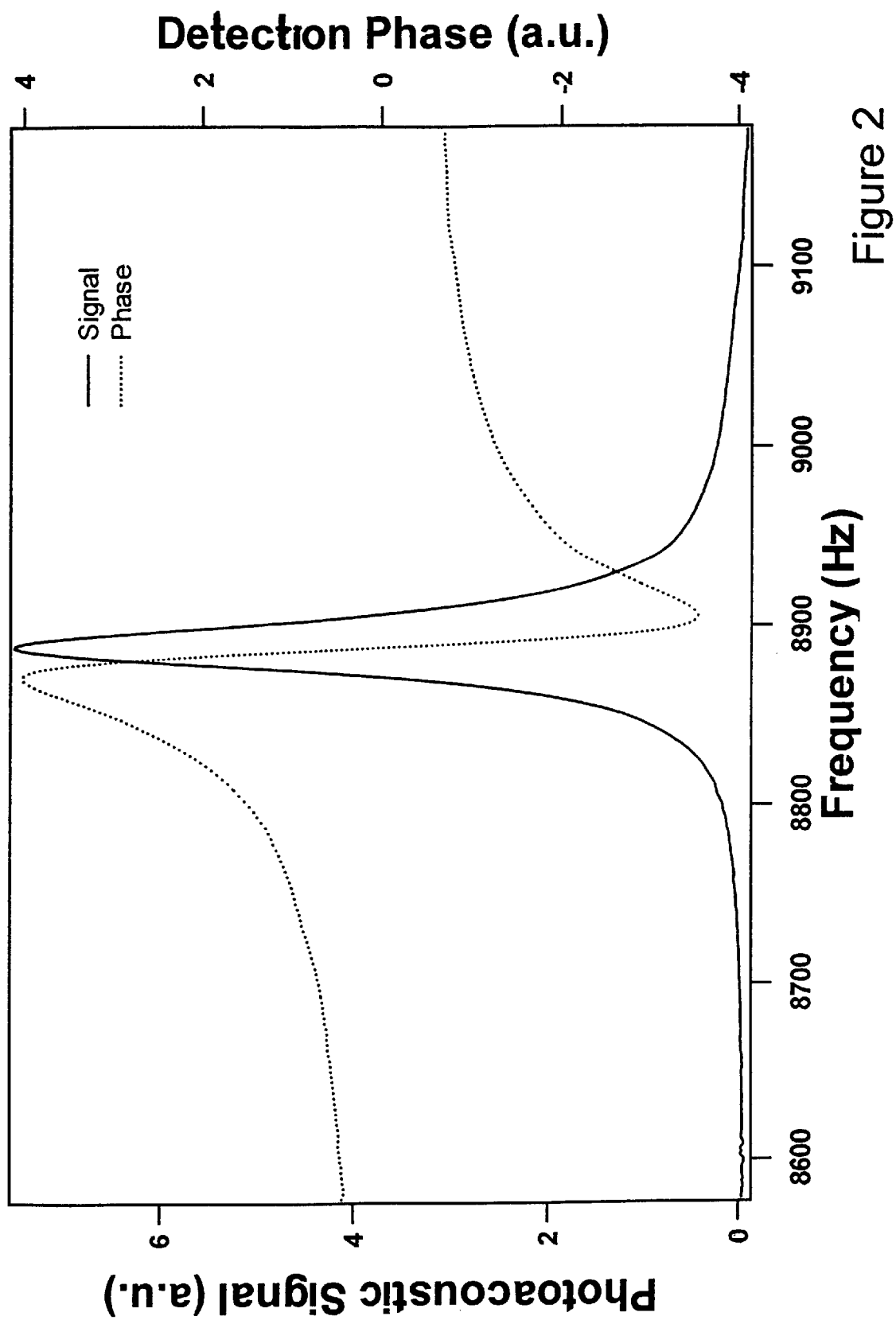
FIG. 2 illustrates the behavior of the detection phase with respect to an acoustic resonance. The data shown are actual experimental data using a wavelength-modulated distributed feedback (DFB) diode laser where the acoustic modulation frequency is swept linearly (triangle sweep) over the cell first radial resonance. Phase and amplitude measurements are made with a digital lock-in amplifier (Stanford Research Systems Model 830).

FIG. 2 shows the spectral profile of a typical photoacoustic cell resonance (radial resonance in this example) and the behavior of the detection phase as a function of acoustic frequency. The behavior is consistent with the requirements for establishing resonance frequency locking. For small deviations from the center of the acoustic resonance, the detection phase is linear in frequency displacement from resonance center. Thus, the magnitude and sign of the detection phase provide the frequency correction necessary to drive the optical source modulation frequency or its harmonics back on to the acoustic resonance center. The present invention permits resonance frequency locking capability using both amplitude modulated optical sources and wavelength modulated optical sources. The wavelength modulated photoacoustic resonance frequency locking was demonstrated using the method of the present invention with the PAS signal determined by an even harmonic of the acoustic modulation frequency.

The lock-in amplifier of FIG. 1 is preferably capable of measuring the detection phase. The detection phase on the lock-in amplifier can be initially adjusted so as to be zero on the resonance center. The detection phase behavior is then consistent with that presented in FIG. 2. If the local detection phase is not adjusted, there will simply be an offset to the detection phase measurement which can be compensated in the resonance locking algorithm. However, a zero crossing at resonance center is preferable. If the lock-in amplifier cannot measure the detection phase, the lock-in amplifier can be adjusted so as to maximize the "in-phase, or X" channel by adjustment of the local lock-in amplifier phase. Then the "out-of-phase, or Y" channel will provide the error signal for resonance frequency locking. This is because the X channel is a maximum on the center of the resonance where the out-of-phase component should be zero (if the local detection phase is adjusted properly). Any change in the detection phase will then show up as a shift of acoustic power from the X channel into the Y channel.

When PAS is implemented with wavelength modulation methods, the present invention for acoustic resonance frequency locking can be used simultaneously with other line locking methods for constraining the optical source wavelength on a gaseous absorption feature. The phase measurement with respect to the acoustic modulation frequency will not impede the ability of a lock-in using an optical detector to maintain the optical source wavelength on the center of the target species absorption center. This combination of absorption resonance line locking with acoustic resonance frequency locking is contemplated by the present invention.

INDUSTRIAL APPLICABILITY

The invention is further illustrated by the following non-limiting examples.

Example 1

Amplitude Modulation

A 1380 nm broadband light emitting diode (LED) was used as the optical source. Amplitude modulation was achieved by 100% square wave modulating the injection current to the LED. Thus, the LED was turned on and off at the injection current modulation frequency. Using a nominal 2" inner diameter cylindrical cell, the first radial resonance was determined to be around 8800 Hz. The acoustic signal was generated by moisture absorption in this wavelength region. The detection phase of the acoustic carrier frequency was used to lock the modulation frequency to the center of the cell acoustic resonance as the moisture content of the air was raised.

Example 2

Wavelength Modulation

A 1392.5 nm single mode distributed feed back (DFB) diode laser was used as the optical source. The laser was utilized to detect moisture. Wavelength modulation was implemented by modulating the laser injection current. DFB lasers scan nearly linearly in wavelength with injection current. Modulation was at one half the first radial resonance frequency, around 4400 Hz, and detected at 2 f or 8800 Hz. When the laser was on the line center of the moisture absorption sound was produced at 2 f which was enhanced by the acoustic cell resonance. Acoustic resonance locking was implemented using the present detection phase method. Also, wavelength modulation of the DFB laser was achieved directly at 8800 Hz and detected at 1 f.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A photoacoustic spectroscopy method for maintaining an acoustic source frequency on a sample cell resonance frequency, the method comprising the steps of:
   providing an acoustic source to the sample cell to generate a photoacoustic signal, the acoustic source having a source frequency;
   continuously measuring detection phase of the photoacoustic signal with respect to a frequency selected from the group consisting of the source frequency and harmonics thereof; and
   employing the measured detection phase to provide magnitude and direction for correcting the source frequency to the resonance frequency.

2. The method of claim 1 wherein the providing step comprises generating sound from absorption of optical power by a species inside the sample cell.

3. The method of claim 2 wherein generating sound from absorption of optical power comprises absorption of optical power modulated by one or more modulating steps selected from the group consisting of amplitude modulating and wavelength modulating.

4. The method of claim 2 wherein generating sound comprises generating sound from absorption of optical power by a flowing gas species.

5. The method of claim 1 wherein the providing step comprises generating sound from a speaker as directed by an external modulator.

6. The method of claim 1 additionally comprising the step of measuring a metric proportional to acoustic power inside the cell.

7. The method of claim 6 wherein the measuring step comprises measuring at a frequency selected from the group consisting of the acoustic source frequency and harmonics thereof.

8. The method of claim 6 wherein in the measuring step the metric is also proportional to a concentration of a species inside the sample cell.

9. A photoacoustic spectroscopy apparatus for maintaining an acoustic source frequency on a sample cell resonance frequency, said apparatus comprising:
   means for providing an acoustic source to the sample cell to generate a modulated photoacoustic signal, said acoustic source having a source frequency;
   means for continuously measuring detection phase of the photoacoustic signal with respect to a frequency selected from the group consisting of the source frequency and harmonics thereof; and
   means for employing the measured detection phase to provide magnitude and direction for correcting the source frequency to the resonance frequency.

10. The apparatus of claim 9 wherein said providing means comprises means for generating sound from absorption of optical power by a species inside the sample cell.

11. The apparatus of claim 10 wherein said means for generating sound from absorption of optical power comprises means for generating optical power modulated by one or more modulations selected from the group consisting of amplitude modulation and wavelength modulation.

12. The apparatus of claim 10 wherein said means for generating sound comprises means for generating sound from absorption of optical power by a flowing gas species.

13. The apparatus of claim 9 wherein the said providing means comprises a speaker and an external modulator.

14. The apparatus of claim 9 additionally comprising means for measuring a metric proportional to acoustic power inside the cell.

15. The apparatus of claim 14 wherein said measuring means comprises means for measuring at a frequency selected from the group consisting of the source frequency and harmonics thereof.

16. The apparatus of claim 14 wherein in said measuring means the metric is also proportional to a concentration of a species inside the sample cell.

17. An acoustic resonance frequency locked photoacoustic spectrometer comprising:
   a source generating a photoacoustic signal, said source having a source frequency; and a lock-in amplifier employing a detection phase of the photoacoustic signal with respect to a frequency selected from the group consisting of source frequency and harmonics thereof, whereby said amplifier maintains said photoacoustic signal on a resonance frequency of a sample cell.

* * * * *